(12) United States Patent
Centanni et al.

(10) Patent No.: US 7,988,920 B2
(45) Date of Patent: Aug. 2, 2011

(54) DEVICE FOR AERATING A REGION AFTER INJECTION WITH VAPORIZED HYDROGEN PEROXIDE

(75) Inventors: Michael A. Centanni, Parma, OH (US); Peter A. Burke, Concord, OH (US)

(73) Assignee: American Sterilizer Company, Mentor, OH (US)

(*) Notice: Subject to any disclaimer, the term of this patent is extended or adjusted under 35 U.S.C. 154(b) by 0 days.

(21) Appl. No.: 12/939,246

(22) Filed: Nov. 4, 2010

(65) Prior Publication Data

US 2011/0052449 A1    Mar. 3, 2011

Related U.S. Application Data

(62) Division of application No. 11/763,574, filed on Jun. 15, 2007, now Pat. No. 7,850,925.

(51) Int. Cl.
*A62B 7/08* (2006.01)
*A61L 9/00* (2006.01)

(52) U.S. Cl. .............. 422/120; 422/30; 422/122

(58) Field of Classification Search ......... 422/30, 422/120, 122
See application file for complete search history.

(56) References Cited

U.S. PATENT DOCUMENTS

| | | | |
|---|---|---|---|
| 2,232,622 A | 2/1941 | Moses et al. | 422/87 |
| 2,741,544 A | 4/1956 | Chalkin et al. | 422/91 |
| 4,046,577 A | 9/1977 | Muzyczko et al. | 96/115 |
| 4,155,895 A | 5/1979 | Rohowetz et al. | 260/33.4 |
| 4,205,043 A | 5/1980 | Esch et al. | 422/56 |
| 4,643,876 A | 2/1987 | Jacobs et al. | 422/23 |
| 4,756,758 A | 7/1988 | Lent et al. | 106/22 |
| 4,756,882 A | 7/1988 | Jacobs et al. | 422/23 |
| 4,843,867 A | 7/1989 | Cummings | 73/23 |
| 4,863,627 A | 9/1989 | Davies et al. | 424/10.32 |
| 4,956,145 A | 9/1990 | Cummings et al. | 422/28 |
| 5,053,339 A | 10/1991 | Patel | 463/2 |
| 5,087,659 A | 2/1992 | Fujisawa et al. | 524/594 |
| 5,139,957 A | 8/1992 | Grack | 436/135 |
| 5,173,258 A | 12/1992 | Childers | 422/27 |
| 5,352,282 A | 10/1994 | Miller | 106/22 |
| 5,420,000 A | 5/1995 | Patel et al. | 430/332 |
| 5,445,792 A | 8/1995 | Rickloff et al. | 422/28 |
| 5,482,684 A | 1/1996 | Martens et al. | 422/119 |

(Continued)

FOREIGN PATENT DOCUMENTS

DE    273 775    11/1989

(Continued)

OTHER PUBLICATIONS

Berka et al., "Kinetics: The Reaction of I⁻ with $H_2O_2$ Using Initial Rate Methods."

(Continued)

*Primary Examiner* — Kevin Joyner
(74) *Attorney, Agent, or Firm* — Kusner & Jaffe; Michael A. Centanni

(57) ABSTRACT

A method and apparatus for aerating a region exposed to a gaseous/vaporous sterilant. A catalytic destroyer and a reactive chemical unit are used to reduce the concentration of the gaseous/vaporous sterilant within the region. The reactive chemical unit includes a chemistry that is chemically reactive with the gaseous/vaporous sterilant. In one embodiment, the gaseous/vaporous sterilant is vaporized hydrogen peroxide and the chemistry of the reactive chemical unit includes thiosulfate and iodide.

8 Claims, 3 Drawing Sheets

U.S. PATENT DOCUMENTS

| | | | |
|---|---|---|---|
| 5,518,927 A | 5/1996 | Malchesky et al. | 436/1 |
| 5,620,656 A | 4/1997 | Wensky et al. | 422/28 |
| 5,770,150 A | 6/1998 | Thornton et al. | 422/61 |
| 5,788,925 A | 8/1998 | Pai et al. | 422/3 |
| 5,789,175 A | 8/1998 | Priest | 436/1 |
| 5,872,004 A | 2/1999 | Bolsen | 435/287.4 |
| 5,872,359 A | 2/1999 | Stewart et al. | 250/339.12 |
| 5,942,193 A | 8/1999 | Bolsen | 422/119 |
| 5,942,438 A | 8/1999 | Antonoplos et al. | 436/1 |
| 5,955,025 A | 9/1999 | Barrett | 422/28 |
| 5,990,199 A | 11/1999 | Bealing et al. | 523/161 |
| 6,063,631 A | 5/2000 | Ignacio | 436/1 |
| 6,087,089 A | 7/2000 | Wu | 435/4 |
| 6,156,267 A | 12/2000 | Pai et al. | 422/3 |
| 6,218,189 B1 | 4/2001 | Antonoplos et al. | 436/1 |
| 6,238,623 B1 | 5/2001 | Amhof et al. | 422/58 |
| 6,267,242 B1 | 7/2001 | Nagata et al. | 206/459.1 |
| 6,287,518 B1 | 9/2001 | Ignacio et al. | 422/86 |
| 6,346,417 B1 | 2/2002 | Ignacio et al. | 436/1 |
| 6,410,338 B1 | 6/2002 | Lippold et al. | 436/166 |
| 6,440,744 B1 | 8/2002 | Ignacio et al. | 436/1 |
| 6,488,890 B1 | 12/2002 | Kirckof | 422/56 |
| 6,551,555 B2 | 4/2003 | Antonoplos et al. | 422/58 |
| 6,790,411 B1 | 9/2004 | Read | 422/28 |
| 7,186,373 B2 | 3/2007 | Centanni | 422/87 |
| 2002/0151084 A1 | 10/2002 | Lippold et al. | 436/163 |
| 2004/0057868 A1 | 3/2004 | McVey et al. | 422/28 |
| 2004/0265170 A1 | 12/2004 | Read | 422/56 |
| 2005/0019206 A1 | 1/2005 | Centanni | 422/3 |
| 2006/0008379 A1 | 1/2006 | Mielnik et al. | 422/32 |
| 2007/0092969 A1 | 4/2007 | Song et al. | 436/1 |
| 2007/0098592 A1 | 5/2007 | Buczynski | 422/3 |
| 2007/0114121 A1 | 5/2007 | Kinlen et al. | 204/175 |
| 2007/0253859 A1* | 11/2007 | Hill | 422/3 |

FOREIGN PATENT DOCUMENTS

| | | |
|---|---|---|
| DE | 273 776 | 11/1989 |
| EP | 0 914 833 | 12/1999 |
| EP | 1 052 507 | 11/2000 |
| JP | 49-46440 | 12/1974 |
| JP | 11-178904 | 7/1999 |
| WO | WO 92/22806 | 12/1992 |
| WO | WO 96/33242 | 10/1996 |
| WO | WO 98/46279 | 10/1998 |
| WO | WO 98/46994 | 10/1998 |
| WO | WO 98/52621 | 11/1998 |
| WO | WO 98/58683 | 12/1998 |
| WO | WO 00/61200 | 10/2000 |
| WO | WO 01/40792 | 6/2001 |
| WO | WO 2005/035067 | 4/2005 |
| WO | WO 2006/046993 | 5/2006 |
| WO | WO 2007/102798 | 9/2007 |

OTHER PUBLICATIONS

Berka et al., "Kinetics: The Reaction of I⁻ with $H_2O_2$ Using Pseudo-Order Methods (Version 1)."

Berka et al., "Kinetics: The Reaction of I⁻ with $H_2O_2$ (Version 2)."

Bishop, "Chapter 8B: Oxidation-Reduction Indicators of High Formal Potential," Indicators, Bishop, ed., Pergamon Press Ltd., Braunschweig, Germany, Title Page, publication page, table of contents, and pp. 531-684 (1972).

Lillie et al., "Ch. 2: The General Nature of Dyes and Their Classification," H.J. Conn's Biological Stains, a Handbook on The Nature and Uses of the Dyes Employed in the Biological Laboratory, 9.sup.th ed., The Williams & Wilkins Company, available from the Sigma Chemical Company, St. Louis, Mo., Title page, publication page, and pp. 19-32, 382-384, and 429-430 (1977).

Shakhashiri, "Hydrogen Peroxide Iodine Clock: Oxidation of Potassium Iodide by Hydrogen Peroxide," Chemical Demonstrations: A Handbook for Teachers of Chemistry, 1992, vol. 4, pp. 37-43.

Extended European Search Report for European Patent Application No. EP 08770552.1, Sep. 7, 2010.

U.S. Appl. No. 12/939,239, filed Nov. 4, 2010, Centanni et al., entitled: Method For Removal of Vaporized Hydrogen Peroxide From a Region.

* cited by examiner

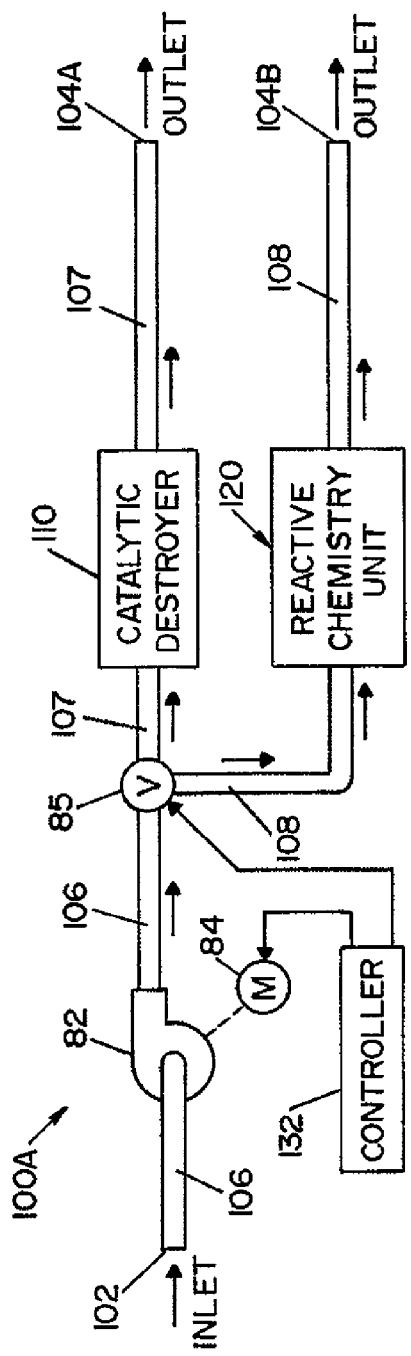
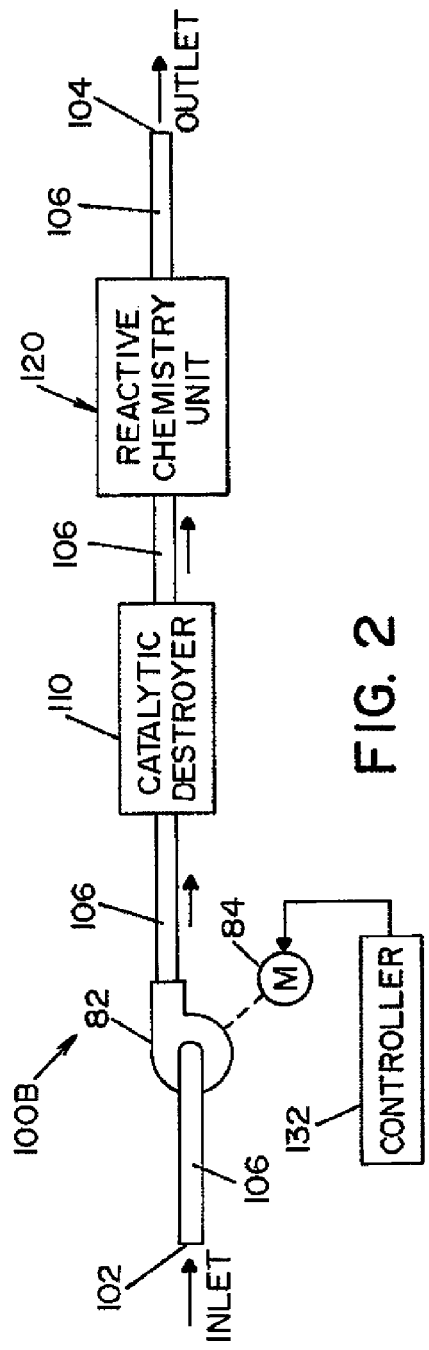

DEVICE FOR AERATING A REGION AFTER INJECTION WITH VAPORIZED HYDROGEN PEROXIDE

RELATED APPLICATIONS

This application is a divisional of U.S. application Ser. No. 11/763,574, filed Jun. 15, 2007 now U.S. Pat. No. 7,850,925 which is fully incorporated herein by reference.

FIELD OF THE INVENTION

The present invention relates generally to the art of sterilization using a gaseous or vaporous chemical agent, and more particularly to a method and apparatus for reducing both large and small concentrations of vaporized hydrogen peroxide in a region by use of a reactive chemistry, such as a reducing agent.

BACKGROUND OF THE INVENTION

An enclosure defining a region (e.g., hotel rooms, offices, laboratories, buildings, cruise ships, airport terminals, and the like) may be sterilized by exposing the region (and any articles therein) to a sterilizing agent, such as vaporized hydrogen peroxide. Vaporized hydrogen peroxide may be generated by vaporizing a metered quantity of an aqueous solution of hydrogen peroxide (e.g., about 30% to 59% hydrogen peroxide, by weight). The vaporized hydrogen peroxide is carried into the region by a carrier gas (e.g., air). As used herein the term "sterilization" includes, but is not limited to, sterilization, disinfection, or sanitization, effecting lethal neutralization of biological contamination, including biowarfare contamination.

The phases of a typical vaporized hydrogen peroxide treatment process include: a drying phase, a conditioning phase, a sterilization phase and an aeration phase. During the drying phase, the region is typically dried to a low humidity level using a dryer (e.g., a desiccant dryer). A conditioning phase follows the completion of the drying phase. During the conditioning phase, vaporized hydrogen peroxide is injected into the region at a relatively high rate to rapidly increase the hydrogen peroxide concentration within the region to an appropriate concentration level. After completion of the conditioning phase, the sterilization phase commences. During the sterilization phase, injection of the vaporized hydrogen peroxide is typically regulated to maintain a substantially constant hydrogen peroxide concentration within the region for a required exposure time. An aeration phase follows the completion of the sterilization phase. During the aeration phase, injection of vaporized hydrogen peroxide into the region is stopped and vaporized hydrogen peroxide is removed from the region until the vaporized hydrogen peroxide concentration is below an allowable threshold level (e.g., 1 ppm).

In certain applications it is advantageous and desirable during the aeration phase to reduce the concentration of vaporized hydrogen peroxide in the region to a level below 1 ppm in as short a time as possible (e.g., fewer than 2 hours), thereby allowing the region to be quickly returned to use. Accordingly, there is a need for a method and apparatus that can effectively and efficiently reduce large concentrations of vaporized hydrogen peroxide in a region to a concentration below the allowable threshold level.

Currently, a catalytic destroyer is often used to reduce the concentration of vaporized hydrogen peroxide by breaking down vaporized hydrogen peroxide into water vapor and molecular oxygen during the aeration phase. Such catalytic destroyers are beneficial in decomposing vaporized hydrogen peroxide concentrations that are above tens of parts per million. However, at low concentrations of vaporized hydrogen peroxide such catalytic destroyers are less efficient at decomposing vaporized hydrogen peroxide into water vapor and molecular oxygen. This may be especially problematic when the air carrying the vaporized hydrogen peroxide is forced through the catalytic destroyer at a high rate, thus reducing the residence time of contact between the elements of the catalytic destroyer (e.g., copper) and the vaporized hydrogen peroxide.

The present invention addresses these and other drawbacks of the prior art, and provides a method and apparatus that effectively and efficiently reduces large and small concentrations of vaporized hydrogen peroxide within a region.

SUMMARY OF THE INVENTION

In accordance with an embodiment of the present invention, there is provided a method for sterilizing and aerating a region, the method comprising the steps of: (a) injecting a gaseous/vaporous sterilant into the region at a sufficient concentration to lethally neutralize biological contaminants contained within the region; (b) maintaining the concentration of the sterilant within the region for a sufficient amount of time to lethally neutralize the biological contaminants contained within the region; and (c) flowing the sterilant through a chemistry that is chemically reactive with the sterilant so that the sterilant reacts with the chemistry to remove the sterilant from the region.

In accordance with another aspect of the present invention, there is provided an apparatus for aerating a region after exposure to a gaseous/vaporous sterilant, the apparatus including a catalytic destroyer having a chemistry that catalytically reacts with the gaseous/vaporous sterilant; and a reactive chemistry unit that includes a chemistry that is chemically reactive with the gaseous/vaporous sterilant.

In accordance with still another aspect of the present invention, there is provided a method for passivating and aerating a region having a chemical contaminant, the method comprising the steps of: (a) injecting a gaseous/vaporous passivating chemical into the region at a sufficient concentration to passivate chemical contaminants contained within the region; (b) maintaining the concentration of the passivating chemical within the region for a sufficient amount of time to passivate the chemical contaminants contained within the region; and (c) flowing the passivating chemical through a chemistry that is chemically reactive with the passivating chemical so that the passivating chemical reacts with the chemistry to remove the passivating chemical from the region.

An advantage of the present invention is the provision of a method and apparatus for aeration wherein concentrations of a gaseous/vaporous sterilant is reduced within a region.

Another advantage of the present invention is the provision of a method and apparatus for aeration that uses reactive chemistry to remove a gaseous/vaporous sterilant from a region.

Still another advantage of the present invention is the provision of a method and apparatus for aeration wherein both large and small concentrations of a gaseous/vaporous sterilant are reduced within a region.

These and other advantages will become apparent from the following description taken together with the accompanying drawings and the appended claims.

BRIEF DESCRIPTION OF THE DRAWINGS

The invention may take physical form in certain parts and arrangement of parts, an embodiment of which will be described in detail in the specification and illustrated in the accompanying drawings which faun a part hereof, and wherein:

FIG. 1 is a schematic view of an aeration system according to a first embodiment of the present invention;

FIG. 2 is a schematic view of an aeration system according to a second embodiment of the present invention;

DETAILED DESCRIPTION OF PREFERRED EMBODIMENT

Figure 3:
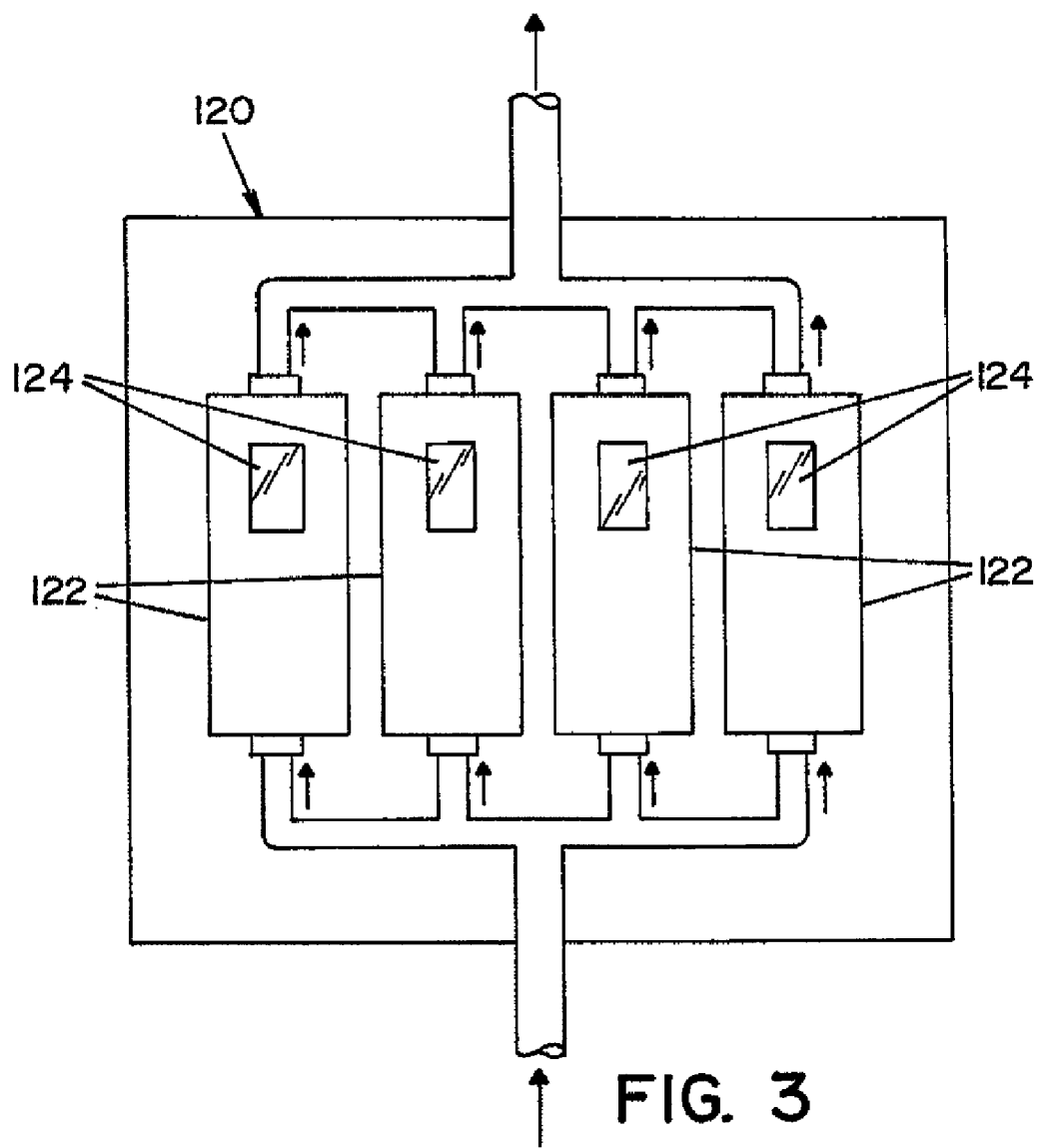
FIG. 3 is a detailed schematic view of a reactive chemistry unit of the present invention according to a first embodiment.

Referring now to the drawings wherein the showings are for the purpose of illustrating embodiments of the invention only, and not for the purpose of limiting same, FIG. 1 shows an aeration system 100A according to a first embodiment of the present invention. Aeration system 100A includes a first conduit 106, a second conduit 107 and a third conduit 108.

A valve 85 is a three-position valve moveable between a first position wherein first conduit 106 is in fluid communication only with second conduit 107, a second position wherein first conduit 106 is in fluid communication only with third conduit 108, and a third position wherein first conduit 106 is in fluid communication with both second conduit 107 and third conduit 108.

An inlet 102 is located at one end of first conduit 106. Inlet 102 is in fluid communication with a region (not shown). A first outlet 104A is located at one end of second conduit 107 and a second outlet 104B is located at one end of third conduit 108. First and second outlets 104A and 104B may be in fluid communication with each other. Furthermore, first and second outlets 104A and 104B may also be in fluid communication with the region, thereby forming a closed loop system comprised of the region and aeration system 100A.

A blower 82, driven by a motor 84, is disposed within conduit 106. A catalytic destroyer 110 is disposed within second conduit 107. Located parallel to catalytic destroyer 110 is a reactive chemistry unit 120 disposed within third conduit 108. Catalytic destroyer 110 and reactive chemistry unit 120 reduce the concentration of vaporized hydrogen peroxide from air withdrawn from the region via inlet 102, as will be described in detail below.

A controller 132 is used to control the operation of aeration system 100A, including motor 84 and valve 85. In this regard, controller 132 may include a programmable microcontroller or microprocessor, a memory or other data storage device, an input means (e.g., a keypad or buttons) and output means (e.g., a display, a speaker and/or a printer).

Catalytic destroyer 110 is a conventional apparatus including a material that reacts catalytically with vaporized hydrogen peroxide. For example, copper or transition metals.

In the illustrated embodiment, reactive chemistry unit 120 is an apparatus including a chemical that chemically reacts with vaporized hydrogen peroxide, such as thiosulfate/iodide chemistry. Accordingly the reactive chemistry unit may include a chemistry comprising an iodide ion (I$^-$), a thiosulfate ($S_2O_3^{2-}$) ion and starch. When this chemistry is exposed to vaporized hydrogen peroxide ($H_2O_2$), the vapor phase hydrogen peroxide ($H_2O_2$) reacts with iodide ion (I$^-$), and hydronium ion (H$^+$) to give a triodide ion (I$_3^-$) and water:

$$H_2O_2 + 3I^- + 2H^+ \rightarrow I_3^- + 2H_2O \tag{1}$$

The thiosulfate ($S_2O_3^{2-}$) reacts quantitatively with the triodide ion (I$_3^-$) and water according to the following reaction:

$$I_3^- + 2S_2O_3^{2-} \rightarrow 3I^- + S_4O_6^{2-} \tag{2}$$

Reaction (2) occurs very rapidly relative to reaction (1). Thus, so long as thiosulfate ($S_2O_3^2$) is present, the triodide ion (I$_3^-$) produced by reaction (1) will be converted back to iodide ion (I$^-$) by reaction (2). Since reaction (2) occurs very rapidly relative to reaction (1), iodide ions (I$^-$) will continue to be produced and exist until the thiosulfate ($S_2O_3^{2-}$) is gone. At that point, triodide ions (I$_3^-$) will accumulate and immediately produce a blue color.

The present invention is described above with respect thiosulfate/iodide chemistry. However, it is contemplated that alternative chemistries, including all reducing agents, reactive with hydrogen peroxide (or other sterilants) may be substituted for the thiosulfate/iodide chemistry.

Figure 4:
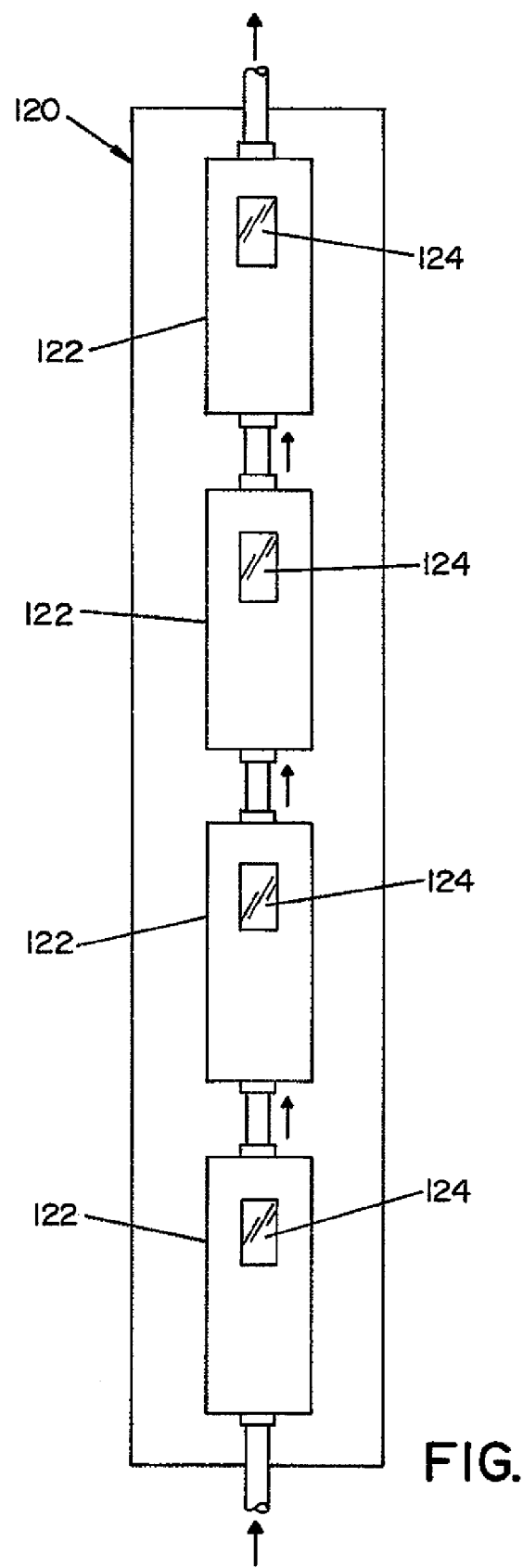
FIG. 4 is a detailed schematic view of a reactive chemistry unit of the present invention according to a second embodiment.

Referring now to FIGS. 3 and 4, two embodiments of reactive chemistry unit 120 are illustrated. In the first embodiment (FIG. 3), reactive chemistry unit 120 is comprised of a plurality of canisters or cartridges 122 arranged in parallel. In the second embodiment (FIG. 4), reactive chemistry unit is comprised of a plurality of canisters or cartridges 122 arranged in series. Cartridges 122 are filled with the chemistry that is reactive with vaporized hydrogen peroxide. In the illustrated embodiment, the chemistry is a liquid solution including iodide ions (I$^-$), thiosulfate ($S_2O_3^{2-}$) ions and starch. In one embodiment of the present invention, reactive chemistry units 120 also include microbubblers or diffusers (not shown) to bubble the air carrying vaporized hydrogen peroxide (i.e., air/vhp) through the liquid solution of thiousulfate/iodide. For example, any number of ceramic microbubblers available from the Nottingham Koi Company (United Kingdom) could be used.

Each cartridge 122 may also include an indicator window 124. As noted above with respect to the thiosulfate/iodide chemistry, when all of the thiosulfate ions ($S_2O_3^2$) have been consumed, no more iodide ions (I$^-$) will be produced. Consequently, the triodide ions (I$_3^-$) of reaction (2) will accumulate and produce a blue color. Indicator window 124 allows the color change of the chemistry to be visible. The color change can be used to indicate that cartridge 122 needs replacement. Alternatively, the reactive chemistry may be in the form of a liquid located inside a container (e.g., a glass or inert container) in which air/vhp is bubbled therethrough.

Where a large volume of air/vhp is to be processed, cartridges 122 are preferably arranged in parallel as shown in FIG. 3, thereby allowing higher volumes of air/vhp to be simultaneously processed. A support structure (not shown) may also be provided to support a bank of cartridges 122.

The reaction rate of the hydrogen peroxide and thiosulfate/iodide chemistry can be increased by increasing the temperature. Accordingly, it is contemplated that reactive chemistry unit 120 may also include one or more heating units for heating cartridges 122. For example, individual heaters may be wrapped around each cartridge 122 to control the temperature of the liquid solution of thiousulfate/iodide. The reaction rate of the hydrogen peroxide and thiosulfate/iodide chemistry can also be increased by adding an appropriate catalyst to the liquid solution of thiousulfate/iodide. An appropriate catalyst includes, but is not limited to, iron (II).

FIG. 2 shows an aeration system 100B according to a second embodiment of the present invention. Aeration system 100B includes a first conduit 106 having an inlet 102 at a first end and an outlet 104 at a second end. Inlet 102 is in fluid communication with a region (not shown). Outlet 104 may be in fluid communication with the region, thereby forming a closed loop system comprised of the region and aeration system 100B.

A blower 82, driven by a motor 84, is disposed within conduit 106. A catalytic destroyer 110 and a reactive chemistry unit 120 are disposed within conduit 106 in series. Catalytic destroyer 110 and reactive chemistry unit 120 are described in detail above in connection with the embodiment of FIG. 1. A controller 132 controls operation of aeration system 100B, including motor 84.

It is contemplated that the aeration system of the present invention may be integrated into a vaporized hydrogen peroxide (vhp) sterilization system used to sterilize an enclosure (e.g., room, laboratory, office, cruise ship, airport terminal, isolator, cabinet, decontamination chamber, or the like) that defines a region.

Operation of aeration system 100A will now be described in detail. Controller 132 activates motor 84, thereby causing blower 82 to draw air carrying vaporized hydrogen peroxide (air/vhp) out of the region and into inlet 102. The air/vhp then travels through first conduit 106. If valve 85 is moved to the first position, then the air/vhp will flow through second conduit 107 and catalytic destroyer 110, before exiting aeration system 100A through outlet 104A. If valve 85 is moved to the second position, then the air/vhp will flow through third conduit 108 and reactive chemistry unit 120, before exiting aeration system 100A through outlet 104B. If valve 85 is moved to the third position, then the air/vhp will travel through both second and third conduits 107, 108, thereby flowing through both catalytic destroyer 110 and reactive chemistry unit 120, before exiting aeration system 100A.

Catalytic destroyer 110 is used to reduce the concentration of vaporized hydrogen peroxide in the air/vhp from a large concentration level to a small concentration level (e.g., 10-20 ppm or less). The reactive chemistry unit 120 is used to further reduce the concentration of vaporized hydrogen peroxide in the air/vhp to yet a lower concentration level. Controller 132 controls the operation of valve 85 to select whether the air/vhp will flow through catalytic destroyer 110, reactive chemistry unit 120, or both.

As discussed above, once the reactive component of the reactive chemistry unit 120 (e.g., thiosulfate) is depleted, a color change can be observed by an operator using indicator window 124 of cartridge 122. Furthermore, since the amount of vaporized hydrogen peroxide that can be treated depends on the amount of thiosulfate disposed within cartridge 122, the quantity of thiosulfate disposed therein can be selected so that a predetermined amount of vaporized hydrogen peroxide can be reacted with the reactive chemistry before a color change occurs. Accordingly, cartridges 122 may be configured so that a residual vaporized hydrogen peroxide concentration level is achieved within the region when the reactive chemistry is depleted and a color change occurs. The approximate residual vaporized hydrogen peroxide concentration level at the time of a color change is determined from: (a) the concentration of vaporized hydrogen peroxide existing in the region after treatment with only catalytic destroyer 110, (b) the volume of the region (i.e., the product of (a) and (b) giving the total initial amount of VHP within the region before treatment with reactive chemistry unit 120), and (c) initial concentration of the reactive chemistry (e.g., thiosulfate) located in each cartridge 122. Therefore, once the reactive chemistry has undergone a color change, an operator will know the approximate residual concentration of vaporized hydrogen peroxide in the region. The concentration of vaporized hydrogen peroxide existing in the region after treatment with only catalytic destroyer 110 may be obtained from simulated laboratory experiments or calculations.

As noted above, the change in color of the reactive chemistry of cartridge 122 acts as an indicator itself as to the approximate concentration of vaporized hydrogen peroxide in the region after treatment by the aeration system of the present invention. It will be appreciated that the residual vaporized hydrogen peroxide concentration level will be approximate, since factors, such as the type of material constituting the enclosure of the region, and articles located within the region (e.g., furniture, flooring, and the like), will have different desorption rates and thus may affect the final approximate concentration of vaporized hydrogen peroxide within the region following treatment with only catalytic destroyer 110.

A chemical change induced by the reactive chemistry may be detected or quantified where the by-product of the chemical reaction is detectable by use of potentiometric, spectrophotometric, spectrometric or chromographic methods. In this regard, a reaction endpoint can be detected either potentiometrically or via chromatography using a calibrated redox reaction, or secondly via direct detection of the reaction by-product. The precise concentration in both cases can be achieved by integrating the peak high or area under the curve of the by-product. Furthermore, the reactive chemistry may induce a chemical change that can be detected or quantified by either potentiometric, spectrophotometric, spectrometric or chromographic methods, to indicate an approximate final concentration of the sterilant within the region.

In accordance with a first operating mode of aeration system 100A, valve 85 is moved to the first position, thereby putting conduit 106 in fluid communication with conduit 107. Therefore, large amounts of inlet air/vhp with high concentrations of vaporized hydrogen peroxide are treated by catalytic destroyer 110. This operating mode reduces the concentration of vaporized hydrogen peroxide from a high value to a low value. Thereafter, valve 85 is moved to the second position, thereby putting conduit 106 in fluid communication with conduit 108. Therefore, the flow of inlet air/vhp is directed to reactive chemistry unit 120 having the reactive chemistry described above. The air/vhp is now treated with the reactive chemistry to further reduce the concentration of vaporized hydrogen peroxide in the inlet air/vhp.

In accordance with a second operating mode of aeration system 100A, valve 85 is moved to the third position, thereby putting conduit 106 in fluid communication with both conduit 107 and conduit 108. Accordingly, air/vhp is treated simultaneously by both catalytic destroyer 110 and reactive chemistry unit 120. In the second operating mode of aeration system 100A, the time to reduce the vaporized hydrogen peroxide concentration is minimized.

The first operating mode discussed above may be used in connection with a method for sterilizing a region with a gaseous/vaporous sterilant and aerating the region thereafter. In this method, gaseous/vaporous sterilant is injected into the region at a sufficient concentration to lethally neutralize biological contaminants contained within the region. The concentration of the gaseous/vaporous sterilant is maintained within the region for a sufficient amount of time to lethally neutralize the biological contaminants within the region. Thereafter, the gaseous/vaporous sterilant remaining in the region is initially flowed through catalytic destroyer 110 by moving valve 85 to the first position. After reducing the concentration of the gaseous/vaporous sterilant to a lower level, the remaining gaseous/vaporous sterilant is flowed through reactive chemistry unit 120 by moving valve 85 to the second position. Reactive chemistry unit 120 further reduces the concentration of the gaseous/vaporous sterilant.

With respect to aeration system 100B, inlet air/vhp passes in series through both catalytic destroyer 110 and reactive chemistry unit 120. Accordingly, the concentration of vaporized hydrogen peroxide in the inlet air/vhp is sequentially reduced by catalytic destroyer 110 and reactive chemistry unit 120.

In the illustrated embodiment of the present invention, the sterilant is vaporized hydrogen peroxide and the reactive chemistry includes iodide ions (I), thiosulfate ($S_2O_3^{2-}$) ions and starch. However, it is contemplated that the present invention may find advantageous application with other gaseous/vaporous sterilants, and chemistries that are reactive to such gaseous/vaporous sterilants. By way of example and not limitation, the gaseous/vaporous sterilant may take the form of: ozone, chlorine dioxide, vaporized bleach, vaporized peracetic acid, vaporized peracid, ethylene oxide, ammonia gas, and vaporized alcohol (e.g., a tertiary alcohol).

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, it is contemplated that the present invention may also be used in connection with processes for passivation of chemical contaminants, including chemical warfare contaminants. It is intended that all such modifications and alterations be included insofar as they come within the scope of the invention as claimed or the equivalents thereof.

Having described the invention, the following is claimed:

1. A device for aerating a region after injection with vaporized hydrogen peroxide, the device including:

a catalytic destroyer having a chemistry that catalytically reacts with the vaporized hydrogen peroxide to reduce the concentration of the vaporized hydrogen peroxide in the region; and one or more replaceable cartridges filled with a liquid solution comprised of a reactive chemistry that chemically reacts with the vaporized hydrogen peroxide to measurably reduce the concentration of the vaporized hydrogen peroxide in the region, wherein said reactive chemistry undergoes a color change only when a component of the reactive chemistry is fully consumed due to reaction with the vaporized hydrogen peroxide, wherein said catalytic destroyer and said one or more replaceable cartridges are disposed in series in a fluid flow pathway receiving air withdrawn from said region to sequentially reduce the concentration of vaporized hydrogen peroxide in the air, said catalytic destroyer located upstream of said reactive chemistry unit.

2. A device according to claim 1, wherein said device includes a heating unit for heating the liquid solution of at least one of said replaceable cartridges.

3. A device according to claim 1, wherein at least one of said replaceable cartridges includes an indicator window for viewing said color change of the reactive chemistry.

4. A device according to claim 1, wherein said color change is indicative of an approximate final concentration of the vaporized hydrogen peroxide within the region.

5. A device according to claim 1, wherein each replaceable cartridge includes a microbubbler for bubbling air carrying the vaporized hydrogen peroxide through said liquid solution comprised of said reactive chemistry.

6. A device according to claim 1, wherein said reactive chemistry that is chemically reactive with the vaporized hydrogen peroxide includes thiosulfate.

7. A device according to claim 6, wherein said liquid solution includes a catalyst for increasing the reaction rate of the vaporized hydrogen peroxide and the thiosulfate.

8. A device according to claim 7, wherein said catalyst includes iron (II).

* * * * *